(12) United States Patent
Sugita et al.

(10) Patent No.: US 7,947,876 B2
(45) Date of Patent: May 24, 2011

(54) PLANT AND PLANT STORAGE ORGAN HAVING GLP-1 DERIVATIVE ACCUMULATED THEREIN AND METHOD OF PRODUCING THE SAME

(75) Inventors: Koichi Sugita, Tokyo (JP); Saori Kasahara, Tokyo (JP); Hiroyasu Ebinuma, Tokyo (JP); Humio Takaiwa, Tsukuba (JP); Hiroshi Yasuda, Tsukuba (JP); Takahito Jomori, Nagoya (JP); Yuji Hayashi, Nagoya (JP); Akira Tashita, Nagoya (JP)

(73) Assignees: Nippon Paper Industries Co., Ltd., Tokyo (JP); Sanwa Kagaku Kenkyusho Co., Ltd., Aichi (JP)

( * ) Notice: Subject to any disclaimer, the term of this patent is extended or adjusted under 35 U.S.C. 154(b) by 543 days.

(21) Appl. No.: 11/662,650

(22) PCT Filed: Sep. 14, 2004

(86) PCT No.: PCT/JP2004/013370
§ 371 (c)(1),
(2), (4) Date: Dec. 21, 2007

(87) PCT Pub. No.: WO2006/030492
PCT Pub. Date: Mar. 23, 2006

(65) Prior Publication Data
US 2008/0292732 A1    Nov. 27, 2008

(51) Int. Cl.
*A01H 5/00* (2006.01)
*C12N 15/82* (2006.01)

(52) U.S. Cl. .................. 800/298; 800/295; 800/288

(58) Field of Classification Search .................. None
See application file for complete search history.

(56) References Cited

U.S. PATENT DOCUMENTS
2004/0146985 A1    7/2004   Sun et al.
2006/0194720 A1*   8/2006   Hayashi et al. .......... 514/12

FOREIGN PATENT DOCUMENTS
| EP | 1 408 050 A1 | | 4/2004 |
| JP | 10-075789 | | 3/1998 |
| WO | WO 98/21348 | * | 5/1998 |
| WO | WO 99/16890 | * | 4/1999 |

OTHER PUBLICATIONS

Egel-Mitani et al. Yield improvement of heterologous peptides expressed in yps1-disrupted *Saccharomyces cerevisiae* strains. (2000) Enzyme and Microgiol. Technology; vol. 26; pp. 671-677.*
Sugita, Koichi et al., "Insulin Bunptisu Sokushin Peptide GLP-1 o Kodo Shuseki shita Senbatsu Marker Free Idenshi Kumikae Ine Shushin no Sakushutsu", Dai 26 The Molecular Biology Society of Japan Nenkai Program, 2003, p. 793.
Hoda Hiroshi et al., "Ine Hainyuchu deno Kinosei Peptide no Hatsugen oyobi Chikuseki", Dai 45 Kai The Japanese Society of Plant Physiologists Nenkai Yoshishu, Mar. 2004, p. 307.
Takaiwa, Fumio et al., Kinosei Seibun o Sakumotsu Kashokubu ni Chikuseki Saseru Food Design, Kagaku to Kogyo, vol. 78, Apr. 2004, pp. 188-196.
Hinke, Simon A. et al., "[Seri$^2$]- and [Ser(P)$^2$] Incertin Analogs", Comparison of Dipeptidyl Peptidase IV. Resistance and Biological Activities in Vitro and in Vivo, The Journal of Biological Chemistry, vol. 279, No. 6, Feb. 6, 2004, pp. 3998-4006.
"Development of Rice Containing Peptide Having a Function of Controlling Blood Glucose", Sanwa Kagaku Kenkyusho Co. Ltd. Research Dept. Drug Development Research Center, Brain Techno News, No. 99, 2003, pp. 10-13, including partial English translation.
"Trypsin: EC3.4.21.4", Seikagaku Jiton 3$^{rd}$ Edition, Kabushiki Kaisha Tokyo Kagaku Dojin, 1998, p. 989.

* cited by examiner

*Primary Examiner* — Cathy Kingdon Worley
(74) *Attorney, Agent, or Firm* — Foley & Lardner LLP

(57) ABSTRACT

The present invention is regarding plants and plant storage organs thereof in which GLP-1 derivatives are accumulated, and methods of producing them. The transgenic plants and plant storage organs thereof accumulate tandem repeated GLP-1 derivatives cleavable with intestinal digestive enzyme to monomeric molecules and are produced by methods comprising: integrating into vectors linked DNAs which comprise tandem repeated DNAs encoding the GLP-1 derivative with trypsin resistance in which the amino acid in the 26th position is Gln, the amino acid in the 34th position is Asn or Asp, and C-terminal consists of Arg or Lys to produce monomeric molecules; introducing the vectors into plant cells; and redifferentiating the obtained transformants. The edible transgenic plants and plant storage organs are useful for treating diabetes and can be ingested by diabetic patients.

16 Claims, 5 Drawing Sheets

Construction of a constructed gene

Expression of 5 GLP-1 derivatives-linked peptide by 2.3k pGluB-SP(GluB)-mGLP-1x5-GluB3'

Confirmation by electrophoresis patter (upper column) and by western blotting (bottom column)

Confirmation of GLP-1 derivative expression by 2.3k pGluB-SP-mGLP-1(6xHis-KDEL)-GluB terminator Confirmation of GLP-1 derivative expression by 2.3k pGluB-PREE99 (mGLP-1x5)-GluB3'

Extraction of one-half grain of ripened seed with 500 μl of 8 M urea buffer
Antibody: anti-mGLP-1, SDS-PAGE 15% gel Extraction of one-half grain of ripened seed with 500 μl of 8 M urea buffer
Antibody: anti-mGLP-1, SDS-PAGE 12.5% gel GLP-1 derivative content in rice expressing 5 GLP-1 derivatives-linked peptide Activity of 5 GLP-1 derivatives-linked peptide after thermal treatment Hypoglycemic effect of rice expressing 5 GLP-1 derivatives-linked peptide in a normal mouse
a) change of glucose level
b) area under the glucose level curve Hypoglycemic effect of rice expressing 5 GLP-1 derivatives-linked peptide in a KKA$^Y$ mouse
a) change of glucose level
b) area under the glucose level curve

PLANT AND PLANT STORAGE ORGAN HAVING GLP-1 DERIVATIVE ACCUMULATED THEREIN AND METHOD OF PRODUCING THE SAME

TECHNICAL FIELD

The present invention relates on a wide range from pharmaceutical fields to food fields, and relates to a transgenic plant or a plant storage organ obtained therefrom, in which GLP-1 derivatives are accumulated, a method for producing the same, and further to a pharmaceutical composition, a food or drink material, or a food or drink for treatment or prevention of diabetes produced by using as a material the plant or the plant storage organ.

BACKGROUND ART

A GLP-1 (glucagon-like peptide-1) is known as a hormone which is secreted from a digestive tract by food intake and acts on the pancreas to stimulate glucose-dependent insulin secretion. In Type 2 diabetic patients, it is reported that responsiveness to this GLP-1 is maintained, while the production of GLP-1 is impaired. It is expected that development of a GLP-1 agent will lead to the application of the agent to a therapeutic agent for diabetes as an insulin secretion promoter to compensate the lack of the GLP-1.

However, the active substance of the GLP-1 is a polypeptide of GLP-1 (7-36) amide or GLP-1 (7-37), which is digested and degraded by a digestive enzyme in the gastrointestinal tract and does not function sufficiently, when the GLP-1 is taken orally. Therefore, in the present state, intravenous injection by instillation or subcutaneous injection is attempted in clinical practice. Moreover, it is also reported that: the GLP-1 is also subjected to degradation by a dipeptidylpeptidase IV (DPP-IV) which exists in blood and tissues, so the active half-life time of the GLP-1 is so short as 1-2 min, and GLP-1 is easily excreted from the kidney, so its half-life time in blood is within 5 min, all of which prevents the GLP-1 from clinical application. Hence, a GLP-1 derivative with a long half-life which is not easily degraded has been developed. For instance, followings are included: the $8^{th}$ position of amino acid substituted derivative (Diabetologia 41: 271-278 (1998); Biochem 40: 2860-2869 (2001)), an amino acid modulator at N- and C-terminals (WO9808871 etc.), a derivative in which Arg is substituted for the amino acid at its $34^{th}$ position and its $26^{th}$ position of Lys is introduced with lipophilic group (WO0007617), and a derivative by amino acid substitution covering all over the sequence (WO9943705 and WO9111457). Further, development of a sustained-release injection preparation which is subcutaneously absorbed slowly, etc. has been performed. However, as they are injection preparations, considering the burden to patients, a GLP-1 to be administered via an alternative route other than injection has been longed.

Production of pharmaceuticals, clinical diagnostics and industrial materials using genetic engineering technique has greatly contributed to the actual industrial world already, among which substance production systems are particularly widely utilized where cultured cells of microorganisms or mammals are used as host cells. However, culture of these cells requires culture facilities and culture media in completed sterile environment, which causes high cost. In addition, mammal cells cannot be used as hosts without involving the risk of contamination of virus which is harmful to human body. Consequently, substance production systems using cheap and safe transgenic plants have been developed instead of substance production systems by culture of cells of microorganisms or mammals. For instance, generation of transgenic plants producing: a high-molecular compound such as biodegradable polyester (e.g. Japanese Laid-Open Patent Application No. 2002-262886), a protein such as a vaccine (e.g. G. Jaeger et al., Eur. J. Biochem. 259, 426, 1999) and lactoferrin (D. Chong et al., Transgenic. Res. 9, 71, 2000), and a peptide such as enkephalin (Japanese-Laid Open Patent Application No. 2000-106890), has been reported so far.

With regard to transgenic plants, production of a functional substance being beneficial to human body in edible parts of the plants e.g. seeds of *Glycine max* or *Oryza sativa*, or vegetable leaves, allows the intended substance to be taken orally into human body directly without an extraction process for them. Further, for seeds, preservation or transportation in facility with refrigerating device is not required, while it can be steadily stored for long time at room temperature. In addition, even when the intended substance is extracted, it can be easily purified, because, unlike leaves, the contamination of phenolic substances seldom occurs with seeds. Accordingly, a seed has been regarded as an ideal organ to produce the intended genetic product, and generation of seeds which produced: proteins such as glycinin (T. Katsube et al., Plant. Physiol. 120, 1063, 1999), enzymes such as (1,3-1,4)-β-glucanase (H. Horvath et al., Proc. Nathl. Acad. Sci. USA., 97, 1914, 2000), and peptides such as enkephalin (D. Chong et al., Transgenic. Res., 9, 71, 2000) has been reported so far.

DISCLOSURE OF THE INVENTION

It is approved that GLP-1 is useful for treatment of diabetes. However, as it is a polypeptide, there is no effective administration method other than injection so far. It is necessary to administrate a large amount so that GLP-1 can exhibit its effect by oral administration, which causes a high cost. Therefore, the object of the present invention is to express a large amount of GLP-1 derivatives in a plant which can be taken orally, and to provide a method for orally ingesting GLP-1 derivatives sufficiently by ingesting the plant, in other words, to provide a plant or a plant storage organ in which GLP-1 derivatives are accumulated, and a method for producing the same. Further, the ultimate object of the present invention is to develop a method for orally ingesting GLP-1 derivatives at a low cost, and to use it for treatment of diabetes.

No example of GLP-1 expression in plants has been observed. Moreover, even by introducing a gene by gene recombination, and to attempt expression in a plant body or a plant storage organ, as it is a low molecular peptide consisting of 30 amino acids, it is often recognized as a foreign body, and there was possibility that it would not accumulate. Therefore, in order to realize expression in a large amount while maintaining an appropriate molecular mass, the present inventors prepared an artificial gene encoding a peptide linking several GLP-1 derivatives to introduce the same to a plant. Moreover, arginin (Arg) residue or lysine (Lys) residue to be the recognition site of trypsin and trypsin-like enzyme is placed to the C-terminal of each GLP-1 derivative, so that GLP-1 derivatives which are expressed in linking state become a single GLP-1 derivative by being cleaved with an endogenous trypsin or an enzyme having a trypsin-like activity, while a plant or a plant storage organ in which GLP-1 derivatives are expressed/accumulated, is ingested, digested and absorbed. The present invention has been completed as a result of such background.

That is to say, the present invention relates to a method for producing a transgenic plant or a plant storage organ thereof in which GLP-1 derivatives are accumulated cleavable with a digestive enzyme, comprising: integrating into a vector a linked GLP-1s-DNA which comprises tandem repeated "n" DNAs ("n" being an integer of 3 or more) encoding a GLP-1 derivative consisting of a GLP-1 (7-36) or an amino acid sequence of GLP-1 (7-36) in which one or a few amino acids are deleted, substituted and/or added, and C-terminal consists of Arg or Lys, and having a GLP-1 activity; introducing the vector into a plant cell; and redifferentiating the obtained transformant.

In the present specification, the linked GLP-1s-DNA can be integrated into a vector, by locating in the downstream of a plant storage organ-specific promoter DNA and a DNA encoding a plant storage protein signal peptide sequence. Further, the linked GLP-1s-DNA can be integrated into a vector in the form inserted into a DNA region encoding a variable region of a plant storage protein DNA or in the form of base substitution into it. Moreover, the linked GLP-1s-DNA can be integrated in a vector, together with a cytokinin-related gene, a drug-resistant gene and a removable DNA element, in a position where the cytokinin-related gene and drug-resistant gene can behave together with the removable DNA element and where the linked GLP-1s-DNA would not behave with the removable DNA element. With this third method, by culturing in a drug-supplemented medium and a drug-free medium a plant cell into which a recombinant vector has been introduced to redifferentiate the transformant, a transgenic plant or its plant storage organ wherefrom a marker gene for selection used as an index when introducing the linked GLP-1-DNA into a host cell is removed, can be obtained. Therefore, this method is preferred. These methods for integrating the linked GLP-1s-DNA into a vector can be used in combination.

Moreover, as a GLP-1 derivative to be used, a GLP-1 derivative in which the amino acid in the 26th position of GLP-1 amino acid sequence is replaced with glutamine, and the amino acid in the 34th position is replaced with asparagine or asparatic acid, or a GLP-1 derivative in which the amino acid in the 8th position of amino acid sequence is replaced with serine or glycine is preferable. The number of linkage of DNAs encoding a GLP-1 derivative "n" is preferably 4 to 8, and most preferably 5. There is no specific limitation for plants to be used, while monocotyledon is preferable and *Oryza sativa* can be exemplified.

The present invention further relates to a transgenic plant or a plant storage organ thereof, in which GLP-1 derivatives are accumulated, obtained by performing these methods. The plant or the plant storage organ thereof in which GLP-1 derivatives are accumulated is used as a pharmaceutical composition, a food or drink material, or a food or drink for treatment or prevention of diabetes.

BEST MODE OF CARRYING OUT THE INVENTION

Figure 1:
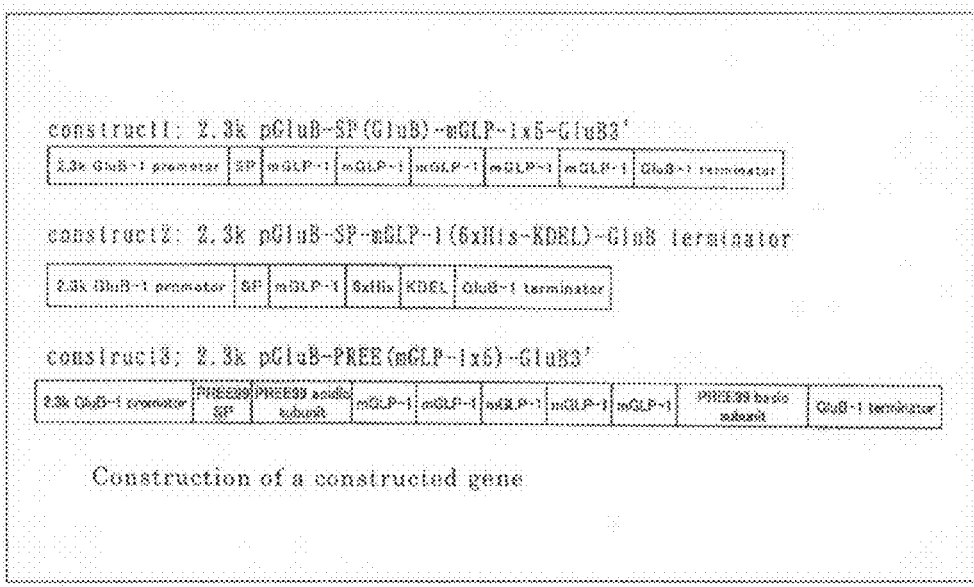
FIG. 1 is a figure showing a gene construction constructed for expressing GLP-1 derivatives. Construct 1 is a gene construct (Test example 1-A) for expressing independently 5 GLP-1 derivatives-linked peptide. Construct 2 is a gene construct (Test example 1-B) for expressing independently a GLP-1 derivative peptide without linkage. Construct 3 is a gene construct (Test example 1-C) for expressing 5 GLP-1 derivatives-linked peptide as a part of glutelin, by introducing a 5 GLP-1 derivatives-linked peptide into a variable region of acidic subunit of glutelin (G1uA-2) which is a main storage protein of Oryza sativa (see for example Test Example 1). 16×His tag disclosed as SEQ ID NO: 7; KDEL disclosed as SEQ ID NO: 8)

The GLP-1 derivative to be used for carrying out the present invention is a GLP-1 derivative comprising GLP-1 (7-36) or its amino acid sequence in which one or a few amino acids are deleted, substituted and/or added, and C-terminal consists of Arg of Lys, and having a GLP-1 activity. In other words, it is a precursor of GLP-1, an analogue of GLP-1, or the C-terminal amide bodies thereof, in which the amino acid of C-terminal consists of Arg or Lys. As such a GLP-1 derivative is orally ingested, it is preferable to be resistant to trypsin and/or dipeptidylpeptidase IV (DPPIV) by amino acid substitution. That is, a trypsin-resistant GLP-1 derivative in which the amino acid in the 26th position of GLP-1 amino acid sequence is replaced with glutamine, and the amino acid in the 34th position is replaced with asparagine or aspartic acid, or a DPPIV-resistant GLP-1 derivative in which the amino acid in the 8th position of the amino acid sequence is replaced with serine or glycine is the most preferred. Among them, a GLP-1 derivative resistant to trypsin and DPPIV, having the both substitutions is most preferable (GLP-1 derivative: SEQ ID No: 1[Ser$^8$, Gln$^{26}$, Asn$^{34}$]-GLP-1).

A DNA encoding the above GLP-1 derivative can be prepared from genome DNA, cDNA, and from chemosynthetic DNA according to an amino acid information of the peptide, and cDNA can be prepared by using methods which are common to a skilled person in the art. Further, DNA synthesis can be appropriately performed by using commercial DNA synthesizers. In doing so, by referring to codons which are commonly used for storage protein gene of plants, it can be modified into the intended DNA by considering degeneracy of amino acids, etc. In case of *Oryza sativa* seeds, a DNA sequence encoding the peptide can be prepared according to codons which are frequently used in the *Oryza sativa* seed storage protein gene, so that it can be translated in *Oryza sativa* seeds effectively.

DNAs of a GLP-1 derivative thus obtained are linked in tandem by common methods. The present invention is characterized by expressing GLP-1 derivatives by linking 3 or more GLP-1 derivatives in tandem. By linking 3 or more GLP-1 derivatives in tandem, stable expression of GLP-1 derivatives can be expected in plant bodies, and plants or plant storage organs containing GLP-1 derivatives at high concentration can be obtained. The number "n" representing the number of linkage of DNAs encoding a GLP-1 derivative is preferably 4 to 8, and most preferably 5.

A DNA of linked-GLP-1 derivatives, that is a linked GLP-1-DNA can be (A) expressed independently, or (B) expressed as a fusion protein by being inserted into a variable region of a plant storage organ protein gene. In the method (A), by recombining it as it is and expressing/accumulating the GLP-1 derivatives independently, it can be expected that it would be not digested when eaten, and be absorbed directly from oral cavity. On the other hand, in the method (B), for example, by inserting it into a variable region of glutelin which is a plant storage protein, and expressing/accumulating the GLP-1 derivatives as a part of glutelin storage protein, it can be expected to be absorbed from the small intestine. In both methods, a linked GLP-1s-DNA can be expressed under control of a plant storage organ specific promoter, by adding a DNA encoding a plant storage protein signal peptide sequence to its 5'-terminal.

In order to express the linked GLP-1s-DNA in plant bodies under control of a plant storage organ specific promoter, a DNA in which a plant storage organ specific promoter and the linked GLP-1s-DNA are linked so that the DNA can be expressed, can be generally introduced into a plant. It is possible to locate a DNA intended to be expressed downstream of a promoter in order to be controlled by the promoter, by using a general genetic engineering technique.

A plant storage organ specific promoter can be used by appropriately selecting or modifying a known promoter, according to the type of a gene intended to be expressed, or to the type of cells into which the gene would be introduced. For example, as a promoter that can be used preferably, a plant storage protein glutelin GluB-1 promoter can be exemplified. Further, glutelin GluB-4 promoter, 26 kD globulin promoter, 10 kD prolamin promoter, and 16 kD prolamin promoter can also be exemplified. The length of these promoters is usually 0.8 kb or more, and preferably 2.3 kb or more. However, there is no particular limitation to the length as long as the promoter has a function. When inserting a linked GLP-1s-DNA into a DNA encoding a plant storage protein, a promoter that is originally located in upstream of the DNA encoding a plant storage organ protein can be used as the above promoter. However, a promoter to be used for controlling a linked GLP-1s-DNA in the present invention is not limited to the above plant storage organ specific promoters, and it may be a promoter such as a plant virus promoter, and it can be appropriately selected according to the plant or plant storage organ in which GLP-1 derivative is intended to be accumulated.

As a plant storage protein signal peptide sequence, various plant storage protein signal peptide sequences that are known can be used appropriately. Amino acid sequence information of a plant storage protein signal peptide sequence can be easily obtained from known references, etc. As a plant storage protein signal peptide sequence, a signal peptide sequence of glutelin (GluB-1) protein can be preferably used. Specifically, it is the sequence MASSVFSRFSIYFCV-LLLCHGSMA (SEQ ID NO: 4). Further, the signal peptide sequence of another glutelin (GluA-2), MASINRPIVFFTV-CLFLLCDGSLA (SEQ ID NO: 5), or the signal peptide sequence of 26 kD globulin, MASKVVFFAAALMAAM-VAISGAQ (SEQ ID NO: 6) can be used. A DNA encoding this plant storage protein signal peptide sequence can be prepared by using commercial DNA synthesizers, etc, considering degeneracy of amino acid sequences, etc. Addition of a DNA encoding a plant storage protein signal sequence to 5'-terminal of the linked GLP-Is-DNA can be performed by using a known genetic engineering technique.

Further, a terminator is added to the 3'-terminal of a linked GLP-1s-DNA, or of a linked GLP-1s-DNA inserted-storage protein DNA. As a terminator, for example, 0.6 kb GluB-1,3' sequence terminator of plant storage protein glutelin, or 0.3 kb 10 kD prolamin terminator can be used for *Oryza sativa*. Moreover, a terminator of nopaline synthase, a terminator of octopin synthase, as well as various terminators of plant genes registered on DNA database can be selected and used.

When the above method (B) for expressing a linked GLP-1s-DNA as a fusion protein by inserting it into a variable region of a plant storage organ is used, 3 regions of the storage protein glutelin acidic subunit GluB-1 of *Oryza sativa* (140, 210, 270 to 310 amino acid regions from N-terminal), and C-terminal region of basic subunit can be exemplified as a variable region. A linked GLP-1s-DNA can be inserted into the gene position encoding each variable region. Moreover, it is possible to insert a linked GLP-1s-DNA one by one to a gene position encoding each of the above variable regions. Meanwhile, glutelin belongs to 11S globulin family (family of glycinin of *Glycine max*, or globulin of *Avena sativa*), and even if it is a protein other than glutelin belonging to this family, a linked GLP-1s-DNA can be inserted to a gene position encoding a variable region such as exemplified above. Further, in case of *Oryza sativa* globulin (family which is different from *Avena sativa* globulin), it is possible to insert a linked GLP-1s-DNA to a gene position encoding a variable region positioned from N-terminal to around 110th amino acid. By referring to one Example of the present method, a method comprising a step of inserting a linked GLP-1s-DNA by basic substitution to the gene region corresponding to the amino acid residue No. 275 to 305 of glutelin Glu A-2 to express a linked GLP-1s-DNA as a part of glutelin, can be exemplified. Insertion of a linked GLP-1s-DNA into a DNA encoding a variable region of a plant storage protein can be performed by a general genetic engineering technique.

Next, a linked GLP-1s-DNA, or a linked GLP-1s-DNA inserted-storage protein DNA is inserted into an appropriate vector together with a plant storage organ specific promoter DNA and plant storage protein signal peptide sequence DNA, and a terminator. The vector is selected from various known vectors by considering appropriately the kind of plant in which it is intended to be expressed, and there is no specific limitation as long as it can retain stably a linked GLP-1s-DNA. A linked GLP-1s-DNA can be inserted into a vector by a ligase reaction using a restriction enzyme site, according to a common method.

A vector in which a linked-GLP-1s-DNA is inserted, is introduced into a plant cell, and a transformed plant cell thus obtained is grown (redifferentiated). As a method of transformation by introducing a vector into a plant cell, several techniques have been already established, including a method for introducing a vector into a protoplast with polyethylene glycol, a method for introducing a vector into a protoplast by electronic pulse, a method for introducing a vector into a cell by particle gun method, and a method for introducing a vector via *agrobacterium*, etc., which techniques are used widely in the technical field. The growth (redifferentiation) of a plant body from a transformed plant cell in which a vector has been thus introduced, can be performed by a known method according to the type of the plant cell. In the present invention, these methods can be used appropriately. When the above *Agrobacterium* method is used, for example, a method of Nagel et al. (Microbiol. Lett., 1990, 67, 325) is used. In this method, by introducing a vector into an *Agrobacterium* bacterium and infecting a plant cell with the transformed *Agrobacterium* by a known method such as leaf disk method, the plant cell is transformed. A plant body being redifferentiated from a transformed cell matures and bears seeds when it is cultivated under a normal cultivation condition after acclimation. Thus, a plant storage organ such as seeds can be obtained.

In doing so, for selecting a transformed plant cell effectively, it is preferable to introduce a vector to be inserted, into a plant cell together with an appropriate selection marker gene or a plasmid vector including a selection marker gene. As a selection marker gene to be used for this purpose, a hygromycin phosphotransferase gene conferring resistance to the antibiotic hygromycin, a neomycin phosphotransferage gene conferring resistance to kanamycin or gentamycin, and an acetyl transferase gene conferring resistance to the herbicide phosphinothricin, etc. can be exemplified.

A plant cell in which a linked-GLP-1s-DNA inserted vector is introduced, is placed on a known selection medium including an appropriate selection drug according to the type of a selection marker gene introduced with the vector, and is cultured. Thus, a transformed plant culture cell can be obtained. However, a drug-resistant gene remains in the obtained plant or plant storage organ, so a problem of safety arises when eating the plant or plant storage organ containing the drug-resistant gene. In order to resolve the problem, a "MAT vector (registered trademark)" described in, for example Bioscience and Industry, Vol. 55 No. 3 (97) 210-212, etc. can be used as a vector for introducing a linked GLP-1s-DNA. In this use, a vector comprising a cytokinin-related gene, a drug-resistant gene, and removable DNA element, wherein a cytokinin-related gene and a drug-resistant gene are located in a position where they can behave together with a removable DNA element, and wherein a DNA in which a DNA encoding a promoter and a signal peptide sequence is added to a linked GLP-1s-DNA, is integrated into a position where it would not behave with the removable DNA element, are preferably used. After introducing the recombinant vector to a plant cell and culturing the same on a drug supplemented medium and drug free medium, a cytokinin-related gene and a drug resistant gene are removed, and thus, a transgenic plant or a plant storage organ without drug resistant gene, in which GLP-1 derivatives are accumulated can be obtained.

As a plant cell to which a vector with a linked GLP-1s-DNA insertion is introduced, any type of plant cells which are reproducible to a plant body are encompassed. For example, leaf, root, stem, flower, plant cells such as germ disk in a seed, callus, and suspension culture cells can be exemplified, but it is not limited to these. When the purpose is to store or replicate the vector, a host cell of the present invention is not necessarily a cell derived from a plant, and can be *E. coli*, yeast, animal cells, etc.

Meanwhile, there is no specific limitation in the present invention for a plant to accumulate therein GLP-1-derivatives by introducing a vector in which a linked GLP-1s-DNA is inserted, and the present invention can be applied to a large number of plants. For example, it is an angiosperm, preferably a monocotyledon, more preferably a plant of *Oryza sativa*. Examples of plants of *Oryza sativa*, cereals including rice, wheat, barley, and corn can be exemplified, while rice is most preferable. Further, by selecting appropriately a promoter to be used, it is possible to accumulate GLP-1 derivatives to various storage organs of these plants, particularly to edible parts. As edible parts vary according to types of plants, it is not necessarily limited, while seed, leaf, and root can be exemplified. More specifically, endosperm in case of rice, wheat, or corn, etc.; cotyledon and germ in case of beans such as *Glycine max*; tuber of potatoes etc., root of carrot, fruits of tomato or banana, etc. can be exemplified. In case of dicots, by using a seed promoter of dicot, for example a cotyledon- or germ-specific promoter, it is also possible to accumulate GLP-1 derivatives in plants such as beans.

Once a transformed plant body of the present invention is obtained, progenies can be obtained from the plant body by a sexual reproduction or asexual reproduction. Moreover it is possible to obtain reproductive materials from the plant body, progeny thereof, or a clone (for example, seed, fruit, cutting, tuber, tuberous root, cell line, callus, protoplast, etc.), and to produce the plant body in a large quantity therefrom.

The plant or plant storage organ thereof obtained as stated above in which GLP-1 derivatives are accumulated is effective as a crop for diabetes treatment, because GLP-1 derivatives can be easily taken in the body when human eats the part thereof. For example, it can provide a pharmaceutical composition for treating or preventing diabetes, including a part (leaf, root, stem, seed, etc.) in which GLP-1 derivatives are accumulated. Further, the part can be provided as a food composition or a food or drink having a preventing/treating effect of diabetes. More specifically, it is a rice obtained by the method of the present invention, in which GLP-1 derivatives are accumulated. Further, a pharmaceutical composition, a food composition, or a food or drink for treating or preventing diabetes including components extracted therefrom, can be exemplified. As a food composition or a food or drink, it can be applied to a cooking method including heating, and further it can be mixed with a compounding ingredient which is acceptable in view of food hygiene and processed as a health food, a functional food, a food for specified health purpose, a nutritional supplement, etc. For example, a compounding ingredient such as a stabilizer, a preservative, a coloring agent, an aroma, a vitamin, etc. can be added appropriately to the above food composition and be mixed to make the food composition in form of tablet, particle, granule, powder, capsule, cream, or liquid, by a common method.

EXAMPLE

The present invention will be described further in detail in the following, while the present invention is not limited to these examples.

Test Example 1

Preparation of a 5 GLP-1 Derivatives-Linked Peptide Expression Plasmid, and Introduction Thereof into *Oriza sativa* "KITAAKE"

To obtain a DNA encoding a peptide of 5-linked GLP-1 derivatives (SEQ ID No:1 of the sequence listing; [Ser$^8$, Gln$^{26}$, Asn$^{34}$]-GLP-1), first, a cDNA encoding the GLP-1 derivative having a blunt end was amplified by PCR using a DNA polymerase (KOD-Plus-, TOYOBO) having a 3'→5' exonuclease activity. The amplified product was self-ligated with T4 DNA ligase (ligation high, TOYOBO) and was introduced into a plasmid (pBS SK+) with a blunt end formed with a restriction enzyme treatment (EcoRV). After *E. coli* was transformed by the obtained plasmid and cultured, a plasmid containing the longest transgene was selected by PCR. Then, isolation of a plasmid and determination of nucleotide sequence were performed to confirm the direction of the cDNA of the linked GLP-1s. By selecting a plasmid in which each cDNA is introduced in the same direction, a 5 linked GLP-1s-DNA encoding a 5 GLP-1 derivatives-linked peptide was obtained.

A. An expression plasmid for expressing a 5 GLP-1 derivatives-linked peptide in *Oryza sativa* seed was prepared by using the above DNA. Specifically, an expression plasmid 2.3 kpGluB-SP(GluB)-mGLP-1×5-GluB-3' (FIG. 1; Construct 1) consisting of a promoter of 2.3-kb glutelin GluB-1 which is a main protein of *Oryza sativa* seed, glutelin signal peptide sequence, 5 GLP-1 derivatives-linked peptide gene, and 0.6-k GluB-1 3' sequence terminator was constructed. The DNA sequence of Construct 1 is shown by SEQ ID No: 2 of the sequence listing, and the amino acid sequence containing a 5 GLP-1 derivatives-linked peptide encoded by the DNA is shown by SEQ ID No:3 of the sequence listing.

B. As a comparison, an expression plasmid, 2.3 k pGluB-SP-mGLP-1(6×His-KDEL)-GluB-terminator (SEQ ID NOS 7 & 8) (FIG. 1; Construct 2), consisting of a promoter of 2.3 kb glutelin GluB-I, glutelin signal peptide sequence, GLP-1 derivative peptide gene, 6×His (SEQ ID NO: 7) tag gene, endoplasmic reticulum anchoring signal KDEL (SEQ ID NO: 8) sequence, and 0.6K GluB-13' sequence terminator, was constructed.

C. By inserting a sequence of the above 5 GLP-1 derivatives-linked peptide gene to a DNA encoding a variable region of an acidic subunit of glutelin (Glu A-2) which is a main storage protein of *Oriza sativa*, an expression plasmid for expressing GLP-1 derivatives as a part of glutelin was produced. In other words, an expression plasmid, 2.3 KpGluB-PREE99(mGLP-1×5)-GluB3' (FIG. 1; Construct 3), consisting of a promoter of 2.3 kb glutelin GluB-1, glutelin signal peptide sequence, glutelin GluA-2 gene PREE99 in which 5 GLP-1 derivatives-linked peptide gene is introduced, and 0.6 k GluB-13' sequence terminator, was constructed. These plasmids were introduced into *Oryza sativa* KITAAKE by *Agrobacterium* method, and a transformant was selected by using hygromycin resistance as an index.

Test Example 2

Figure 2:
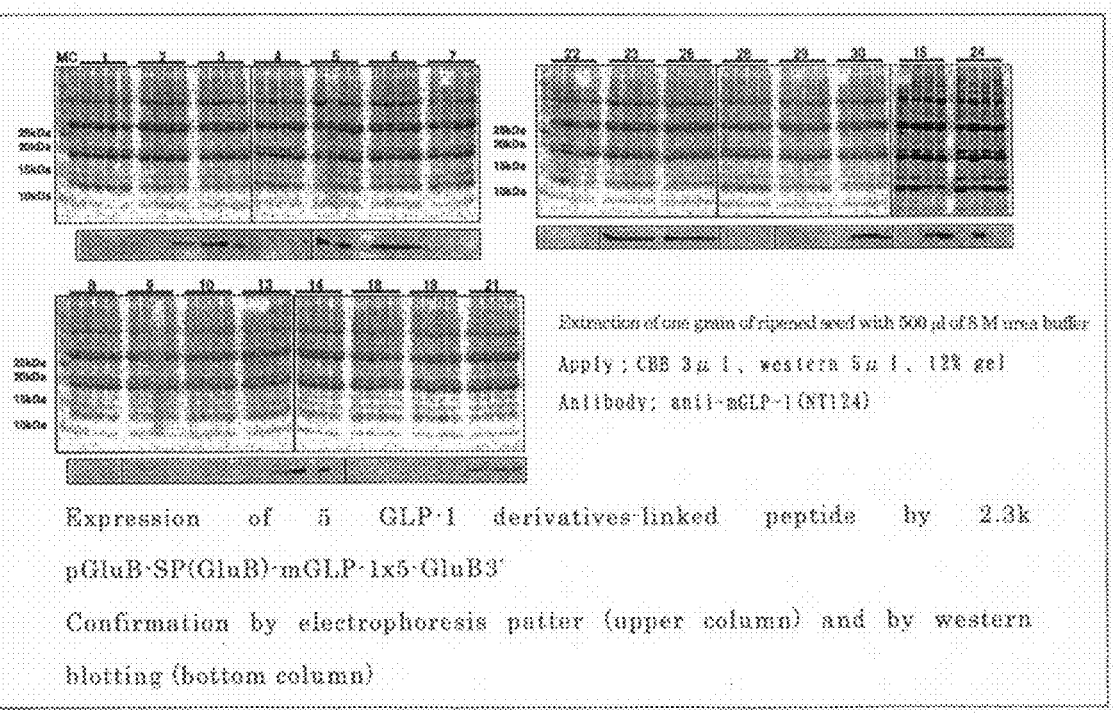
FIG. 2 is a figure showing the analysis result of 5 GLP-1 derivatives-linked peptide of each strain of rice derived from different transgenic Oryza sativa, obtained by introducing Construct 1 (Test example 1-A). 4 grains of each 7 strain were used. The upper column shows electrophoresis pattern, and the bottom column shows the result detecting GLP-1 derivatives by western blotting. Expression of 5 GLP-1 derivatives-linked peptide was observed in No. 2, 3, 5, 6, 14, 21, 23, 26, 30, 15, and 24 (see Test Example 2).

Detection of a 5 GLP-1 Derivatives-Linked Peptide in a Transformant Seed Selected with a Hygromycin-Resistant Gene Seeds of the transformants obtained in Test Example 1, A, B, and C, were analyzed. First, the transformant by 2.3 k pGluB-SP(GluB)-mGLP-1×5-GluB-3' of the above Test Example 1 in which a 5 GLP-1 derivatives gene is introduced was analyzed. The extract solution of ripened seeds obtained from the above transformant was subjected to Western Blotting. A signal estimated to be the 5 GLP-1 derivatives-linked peptide was observed in 11 strains among 23 strains, and the expression of the 5 GLP-1 derivatives-linked peptide was confirmed (FIG. 2).

Figure 3:
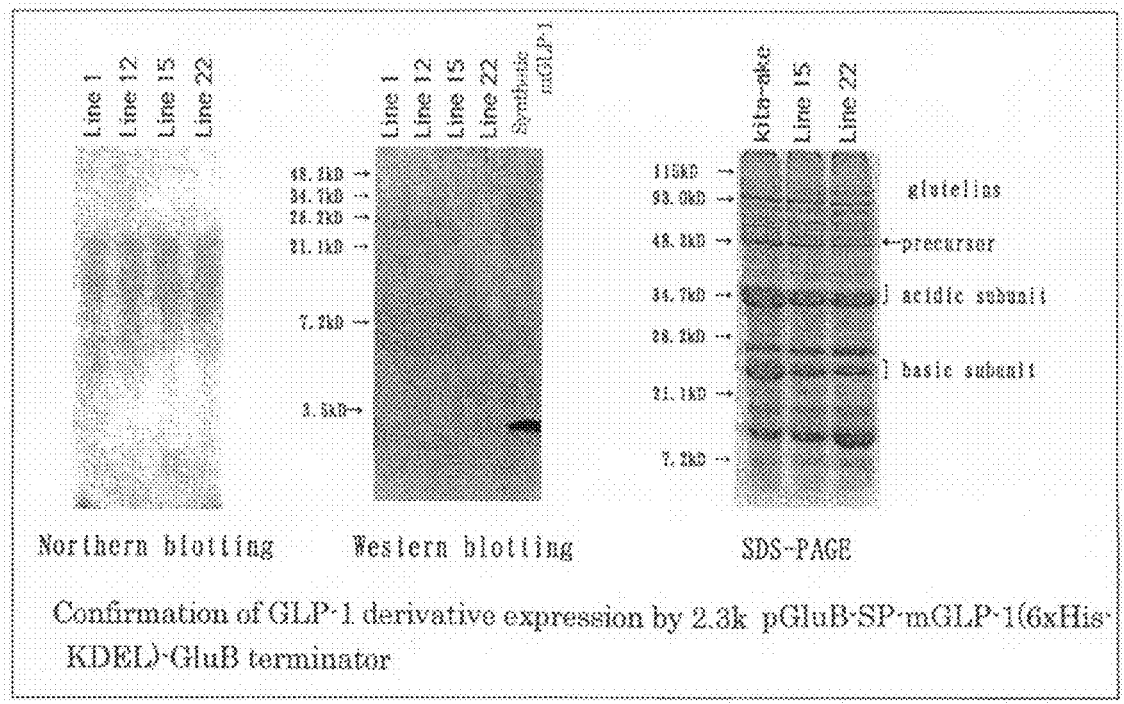
FIG. 3 is a figure showing the analysis result of each strain of rice derived from different transgenic Oryza sativa, obtained by introducing Construct 2 (Test Example 1-B). No signal of GLP-1 derivatives was observed for any of the strains, neither by Northern blotting, western blotting, nor SDS-PAGE electrophoresis. (see Test Example 2). (6×His tag disclosed as SEQ ID NO: 7; KDEL disclosed as SEQ ID NO: 8)

On the other hand, by analyzing 24 strains of the transformant by 2.3 k pGluB-SP-mGLP-1 (6×His-KDEL)-GluB-terminator plasmid vector of the above test example 1-B in which only one GLP-1 derivative gene is introduced, no GLP-1 derivative was detected by Northern blotting, nor by Western blotting (FIG. 3).

Figure 4:
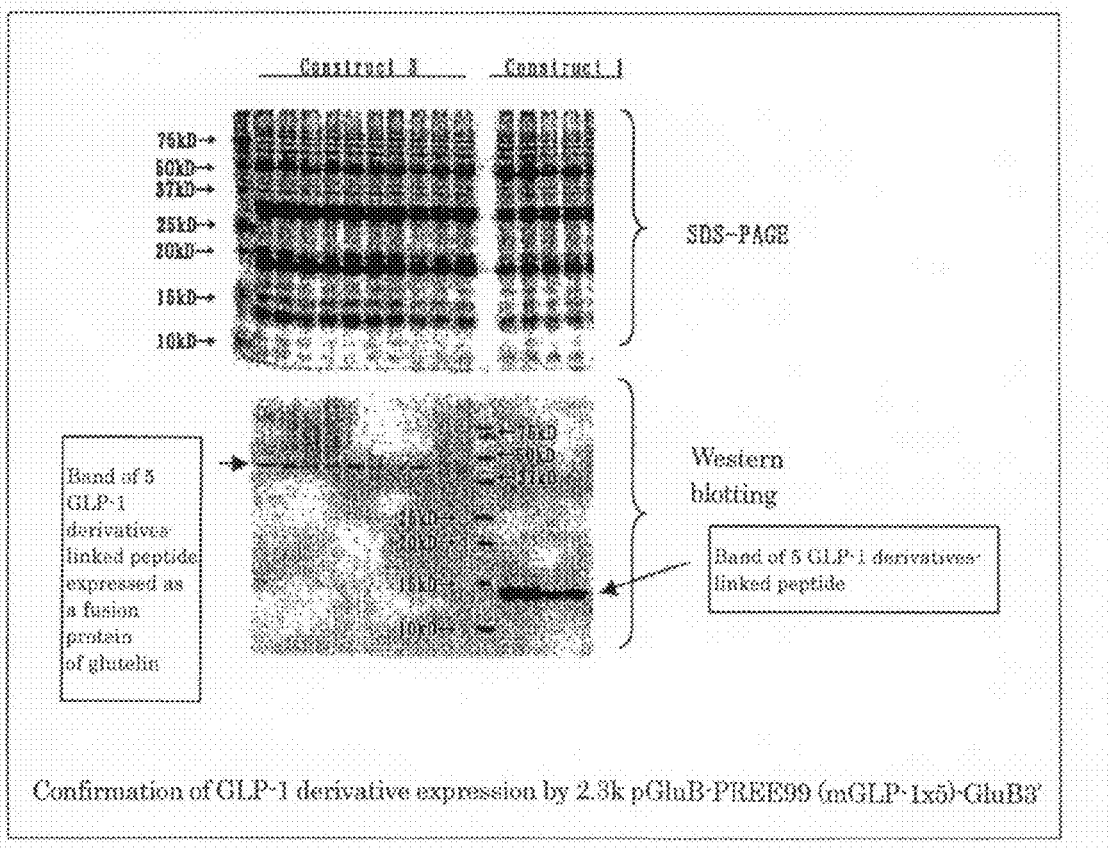
FIG. 4 is a figure showing the analysis result of SDS-PAGE electrophoresis and western blotting for each strain of rice derived from different transgenic Oryza sativa obtained by introducing Construct 3 (Test Example 1-C), by comparing it with Construct 1 (Test Example 1-A). Expression of GLP-1 derivatives was observed in a transformant where it is expressed as a part of glutelin, but the expression level was lower compared to that of Construct 1 (see Test Example 2).

Further, in a transformant by 2.3 k pGluB-PREE99 (mGLP-1×5)-GluB3' of the above Test Example 1-C, which expresses a 5 GLP-1 derivatives-linked peptide as a part of glutelin, expression of the GLP-1 derivatives was observed in 10 strains among 22 strains. However, when comparing the expression level by the signal ratio of Western Blotting, it was ¹/₁₅ or less of that of 2.3 k pGluB-SP(GLuB)-mGLP-1× 5-GluB-3' (Test Example 1-A) which expressed the same 5 GLP-1 derivatives-linked peptide independently (FIG. 4).

From the above results, by linking five GLP-1-derivative genes and expressing it, GLP-1 derivatives were accumulated in rice in a large amount for the first time. As one GLP-1 derivative gene was not expressed solely, it is highly useful to use linked GLP-1s-DNA for expressing GLP-1 derivatives. Further, as for the accumulation level of 5-linked GLP-1 derivatives, the concentration level was higher when it is expressed independently, compared to when it is expressed as a fusion protein by inserting it into a storage protein. One of the reasons for this is thought that a quantitative restriction as a storage protein is less when expressed independently.

Test Example 3

Detection of a 5 GLP-1 Derivatives-Linked Peptide in a Transformant of *Oryza sativa* "NIPPONBARE" Generated with a "MAT Vector" (Registered Trademark)

Figure 5:
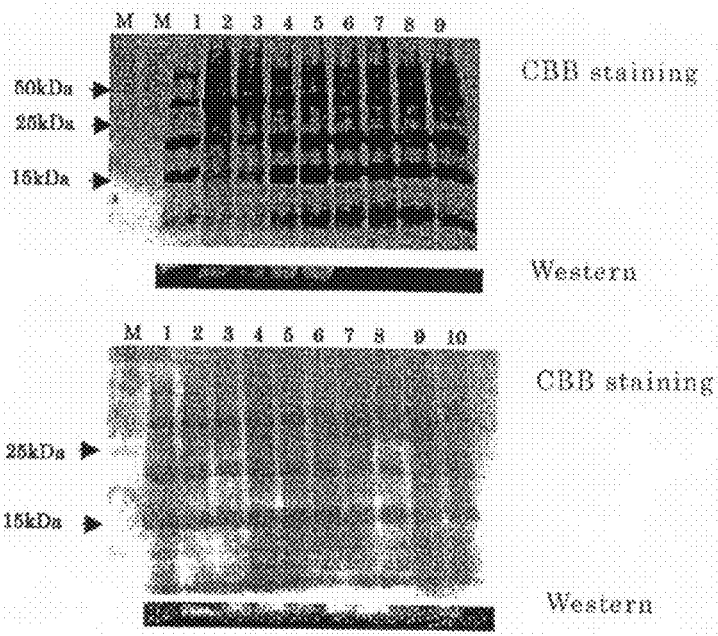
FIG. 5 is a figure showing the analysis result of 5 GLP-1 derivatives-linked peptide of each strain of rice obtained from *Oryza sativa* which expresses introduced pTL7GluB-(mGLP-1×5)-GluBT-130Hm (Test Example 3). The upper column shows electrophoresis pattern, and the bottom column shows the result detecting GLP-1 derivatives by western blotting.
Figure 6:
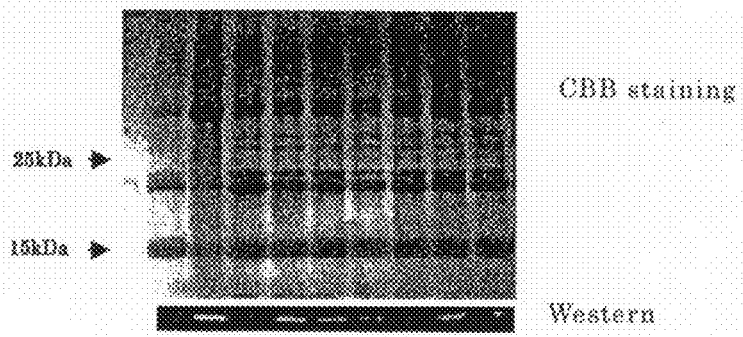
FIG. 6 is a figure showing the analysis result of 5 GLP-1 derivatives-linked peptide of each strain of rice obtained from *Oryza sativa* which expresses introduced pTL7GluB-PREE99(mGLP-1×5)-GluBT-130Hm (Test Example 3). The 8 upper column shows electrophoresis pattern, and the bottom column shows the result detecting GLP-1 derivatives by western blotting.

In a region between two RS sequences (recombinant sequence of a site-specific recombination system) directed in the same direction, R gene (recombinase gene of a site-specific recombination system), ipt gene, and hygromycin phosphotransferase genes are placed, and in the outside of the region between the RS sequences, a "MAT vector (registered trademark)" in which Construct 1 shown in Test Example 1-A or Construct 3 shown in Test Example 1-C is placed, is prepared. The former was named pTL7GluB-(mGLP-1×5)-GluBT-130Hm [International accession number according to Budapest treaty in the International Patent Organism Depositary: FERM BP-10020, at International Patent Organism Depositary, National Institute of Advanced Industrial Science and Technology (address: AIST Tsukuba Central 6, 1-1, Higashi 1-chome Tsukuba-shi, Ibaraki-ken, Japan)], and the latter was named pTL7GluB-PREE99 (mGLP-1×5)-GluBT-130Hm [International accession number according to Budapest treaty in the International Patent Organism Depositary: FERM BP-10021]. Then, these vectors were introduced into *Oryza sativa* "NIPPONBARE" by *Agrobacterium* method, respectively. Selection of a transformant was performed by using hygromycin resistance as an index, and the selected transformants were analyzed. As a result of Western Blotting of the extract solution of ripening seeds obtained from the above transformants, in both the transformant by pTL7GluB-(mGLP-1×5)-GluBT-130Hm and the transformant by pTL7GluB-PREE99 (mGLP-1×5)-GluBT-130Hm, a signal estimated to be the 5 GLP-1 derivatives-linked peptide was observed, and the expression of the 5 GLP-1 derivatives-linked peptide was confirmed (FIGS. 5 and 6).

Test Example 4

Measurement of GLP-1 Content in Rice Expressing GLP-1 Derivatives

The GLP-1 content of GLP-1 derivatives-accumulated rice obtained in the above Test Example 1-A was measured. That is, one grain of rice (with hull) was put in a 2 ml-microtube with packing, and was powdered with a bead shocker (Yasui Kikai) at 2500 rpm, for 10 sec. Then, 1 ml of an extraction buffer (50 mM Tris-HCL buffer solution (pH 6.8) containing 4% sodium dodecyl sulfate, 8M urea, 0.5% 2-mercaptoethanol) was added, and stirred until being dissolved. This dissolved solution was subjected to dialysis (1L×three times) for one day and night at 4° C. with distilled water. The resultant was centrifuged at 15,000 rpm for 5 min, and the supernatant was collected as a GLP-1 derivatives extraction solution.

112 µl of 50 mM ammonium hydrogen carbonate (pH 7.8) and 6 µl of 83 µg/ml trypsin solution (Promega: Cat. No. V5113) were added to 8 µl of the GLP-1 derivatives extraction solution and reacted for 2 hours at 37° C., to make a GLP-1 derivatives linked peptide into monomer GLP-1 derivatives. 462 µl of 95% ethanol was added to stop the reaction, and the supernatant was collected after 15,000 rpm-centrifugation at 4° C. for 5 min, and dried by centrifugal evaporation. The dried material was dissolved and the content was measured with a RIA kit (LINCO, GLP-1 (total) RIA kit).

Figure 7:
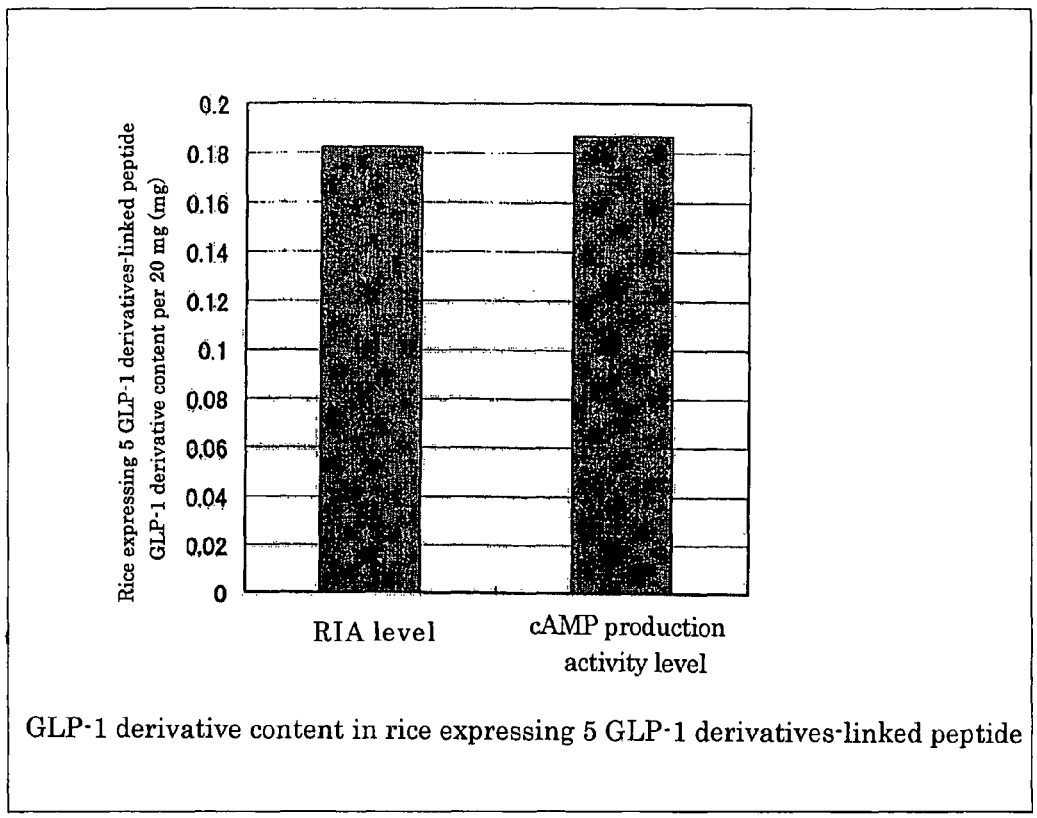
FIG. 7 is a figure showing the content of 5 GLP-1 derivatives-linked peptide in rice obtained from *Oryza sativa* which expresses introduced Construct 1 (Test Example 1-A), measured by radioimmunoassay (RIA) and cAMP production activity (see Test Example 4).

As a result, the highest GLP-1 derivative content in a rice expressing the 5 GLP-1 derivatives-linked peptide (above Test Example 1-A) was 180 µg per 20 mg of rice grain (FIG. 7).

Test Example 5

Figure 8:
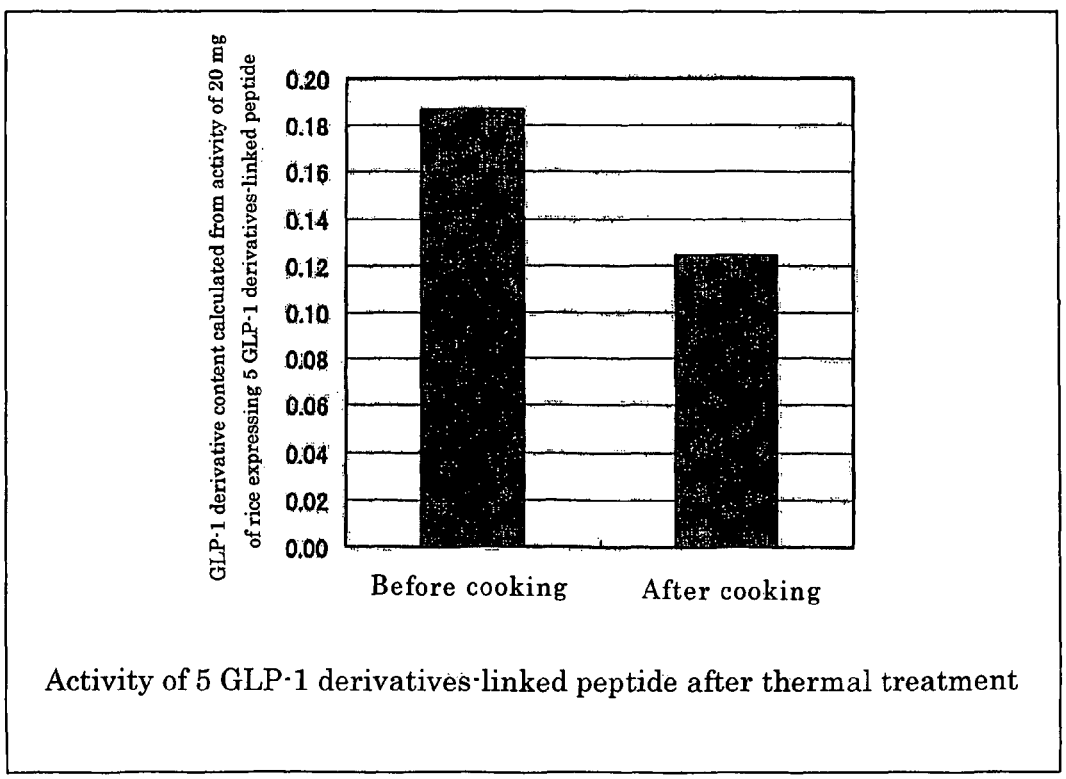
FIG. 8 is a figure showing the investigation result of heat stability of 5 GLP-1 derivatives-linked peptide in rice obtained from *Oryza sativa* which expresses introduced Construct 1 (Test Example 1-A) (see Test Example 5).

Thermal Stability of a 5 GLP-1 Derivatives-Linked Peptide Product Expressed in *Oryza sativa* Seed Thermal stability of the GLP-1 derivative obtained from rice expressing the 5 GLP-1 derivatives-linked peptide and that of native GLP-1 and GLP-1 derivative both obtained by synthesis were compared. Distilled water was added to rice expressing the 5 GLP-1 derivatives-linked peptide (above Test Example 1-A) and extraction was performed in the same manner as in Test Example 4 after thermal treatment for 15 min at 100° C. Further, trypsin treatment was performed, and a monomer GLP-1 derivative was obtained. On the other hand, the synthetic native GLP-1 and the synthetic GLP-1 derivative peptide were made to be 10 µg/ml with 0.2% BSA solution, and thermal treatment was performed for 15 min at 100° C. To these thermal treated substances, non-thermal treated substances were prepared similarly as a control. Then, with respect to these substances, the activity was measured by cAMP generation using mouse islet. As a result, the synthetic native GLP-1 and the synthetic GLP-1 derivative were stable for thermal treatment. The activity of the GLP-1 derivative obtained from expressed rice which was thermally treated was about 33% lower than that of the GLP-1 derivative obtained from expressed rice which was not thermally treated (FIG. 8). From this result, rice expressing GLP-1 derivative of the present invention retained a certain measure of its activity even when it was cooked, and it was estimated that blood glucose lowering effect could be exhibited. On the other hand, as the synthetic peptide was heat-stable, the 5 linked peptide expressed in rice was estimated to have changed by thermal denaturation to a tertiary structure which would not be easily digested by trypsin.

Test Example 6

Blood Glucose Lowering Effect of GLP-1 Derivatives Accumulated Rice in Mice

Blood glucose lowering effect of the rice expressing the 5 GLP-1 derivatives-linked peptide (above Test Example 1-A) was investigated. As control rice, "KITAAKE", the same non-transformed rice as that used for GLP-1 gene introduction, was used. Each rice was milled, immersed, and water in an amount of 3.8 fold of rice weight was added, and cooked at 100° C. for 15 min. Then, rice was crushed and uniformed in a paste form. The Control rice and the rice expressing the 5 GLP-1 derivatives-linked peptide, both containing 100 mg of glucose amount, respectively were fed to normal mice (Crj: ICR, 8 w, male) fasted over night. Meanwhile, the dose of the GLP-1 derivative administered was determined by measuring cAMP generation activity of cooked rice, in the same manner as in Test Example 4, and was calculated to be about 1.0 mg/mouse. The control rice was fed to the positive control group, following subcutaneous administration of 20 µg/kg of the GLP-1 derivative peptide at the dorsal part. On the other hand, to the group fed with the control rice and to the group fed with the rice expressing the 5 GLP-1 derivatives-linked peptide, 5 ml/kg of physiological saline was administered subcutaneously at the dorsal part. Blood glucose level was measured with a Glutest Sensor by collecting blood from tail end before feeding cooked rice and up to 3 hours after feeding with 20 min interval.

Figure 9:
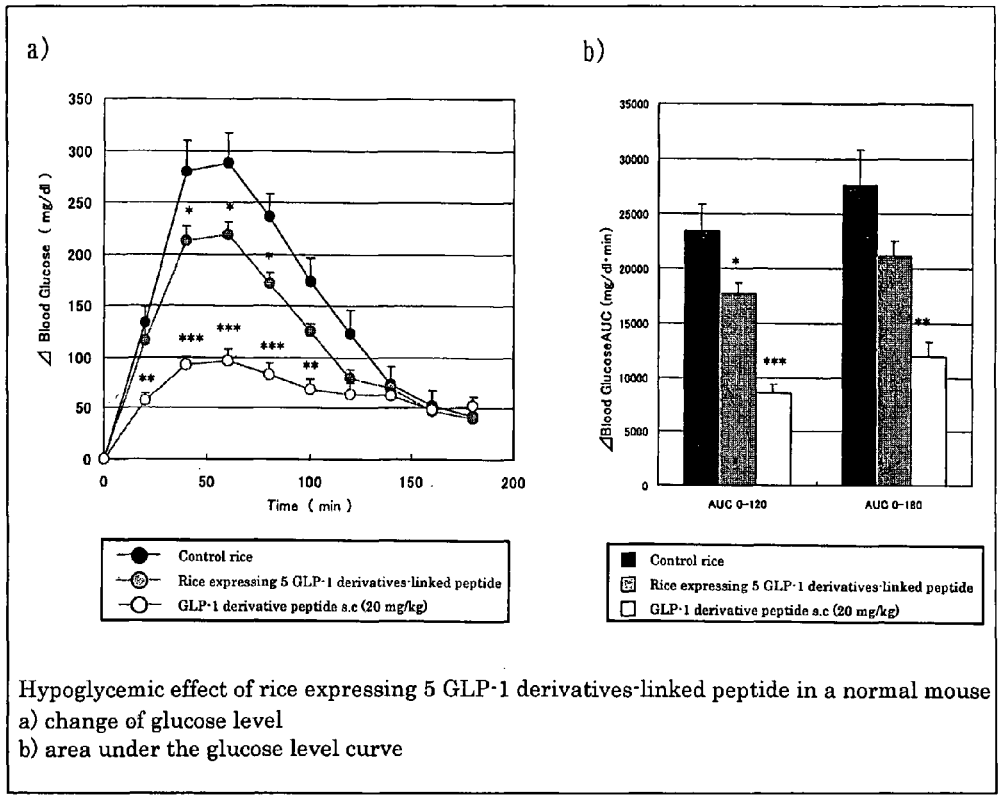
FIG. 9 is a figure showing the investigation result of blood glucose lowering effect in a normal mouse, by using rice obtained from *Oryza sativa* (which expresses 5 GLP-1 derivatives-linked peptide) which expresses introduced Construct 1 (Test Example 1-A) (see Test Example 6).

As a result, it was observed that by feeding the rice expressing a 5 GLP-1 derivatives-linked peptide to a mouse, the blood glucose level from 40 to 80 min and the area under the blood glucose level curve from 0 to 120 min of the group mouse were significantly suppressed compared to those of the control rice-fed group mouse (FIG. 9). Thus, blood glucose lowering effect of the rice expressing a 5 GLP-1 derivatives-linked peptide was confirmed in an animal experiment.

In an experiment separately performed by the present inventors in which a GLP-1 peptide itself was administered orally to a mouse, 50 to 150 µg of the GLP-1 peptide was necessary to obtain a blood glucose lowering effect. From this experiment, when the body weight of human is estimated to be 60 kg, the amount of the GLP-1 peptide necessary to induce blood glucose lowering effect in human is 150 mg to 450 mg. It is necessary to eat 830 to 2490 grains to ingest this amount by eating rice in which 180 µg of the GLP-1 peptide is accumulated per grain. As the number of rice grains in one rice bowl which human eats is from 3000 to 4000 grains, in case of rice of the present invention, it is possible for a person to ingest GLP-1 amount necessary for showing the blood glucose lowering effect with rice grains of one rice bowl.

Test Example 7

Figure 10:
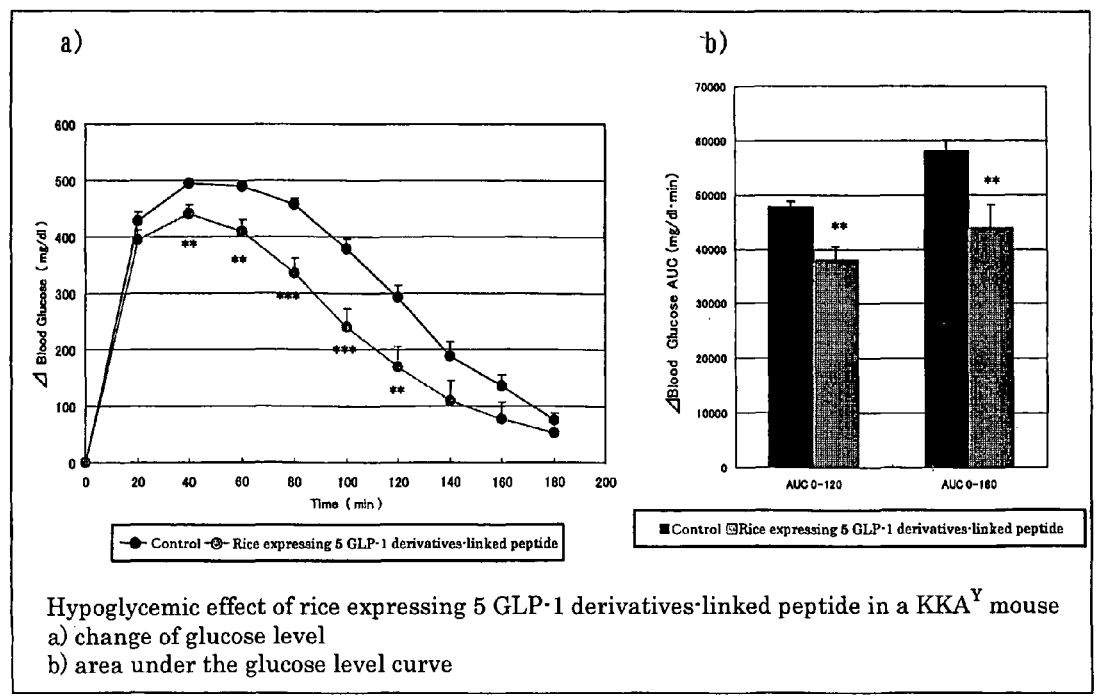
FIG. 10 is a figure showing the investigation result of blood glucose lowering effect in a Type 2 diabetic mouse model KK-AY, by using rice obtained from *Oryza sativa* (which expresses 5 GLP-1 derivatives-linked peptide) which expresses introduced Construct 1 (Test Example 1-A) (see Test Example 7).

Blood Glucose Lowering Effect of Rice Expressing GLP-1 Derivatives in KK-A$^y$ Mouse An test similar to Test Example 6 was carried out with the use of type II diabetes model animal, KK-A$^y$ mouse. The experiment was conducted with the same administration level as the normal mouse of Test Example 5, while the KK-A$^y$ mouse showed a higher glucose level compared to that of the normal mouse of Test Example 5. However, in the group fed with rice expressing a 5 GLP-1 derivatives-linked peptide, a significant suppressing effect was observed compared to the group fed with control rice, and a blood glucose lowering effect of the rice expressing a 5 GLP-1 derivatives-linked peptide was confirmed (FIG. 10). From this result, the effect of the rice expressing a 5 GLP-1 derivatives-linked peptide can be also expected in type II diabetes patients.

As described above, the present inventors accumulated a large amount of GLP-1 derivatives in a plant, and succeeded in developing a plant in which the peptides having therapeutic effect are accumulated, and thus completed the present invention.

INDUSTRIAL APPLICABILITY

The present invention provides a transgenic plant and/or a plant storage organ thereof in which GLP-1 derivatives are accumulated. For example, it provides rice in which GLP-1 derivatives are accumulated. By eating the plant or plant storage organ in which GLP-1 derivatives are accumulated, or extraction component thereof, blood glucose can be lowered, which is useful for diabetes treatment.

The invention claimed is:

1. A transgenic plant or a plant storage organ thereof in which GLP-1 derivatives are accumulated cleavable with a digestive enzyme and which is produced by a method comprising: integrating into a vector a linked DNA which comprises 3 or more tandem repeats of nucleic acids encoding the GLP-1 derivative in which the amino acid in the $8^{th}$ position of the GLP-1 derivative is selected from the group consisting of alanine, serine, and glycine, and in which the amino acid in the 26th position of the GLP-1 derivative is replaced with glutamine, the amino acid in the 34th position of the GLP-1 derivative is replaced with asparagine or aspartic acid, and C-terminal amino acid residue is Arg or Lys; introducing the vector into a plant cell; and redifferentiating a transgenic plant from said plant cell.

2. The transgenic plant or the plant storage organ thereof according to claim 1, wherein the GLP-1 derivative is a GLP-1 derivative in which the amino acid in the $8^{th}$ position of the GLP-1 derivative is serine or glycine.

3. The transgenic plant or the plant storage organ thereof according to claim 1, wherein the number of tandem repeats encoding the GLP-1 derivative is 4 to 8.

4. The transgenic plant or the plant storage organ thereof according to claim 1, wherein the number of tandem repeats encoding the GLP-1 derivative is 5.

5. The transgenic plant or the plant storage organ thereof according to claim 1, wherein the vector comprises a plant storage organ specific promoter operably linked to a nucleic acid encoding a signal peptide of a plant storage protein and the linked DNA.

6. The transgenic plant or the plant storage organ thereof according to claim 1, wherein the vector comprises the linked DNA inserted in-frame into a nucleic acid encoding a variable region of a plant storage protein.

7. The transgenic plant or the plant storage organ thereof according to claim 1, wherein the plant is a monocotyledon.

8. The transgenic plant or the plant storage organ thereof according to claim 7, wherein the monocotyledon is *Oryza sativa*.

9. The transgenic plant or the plant storage organ thereof according to claim 1, wherein the plant storage organ is a seed.

10. The transgenic plant or the plant storage organ thereof according to claim 2, wherein the number of linkage of DNA encoding the GLP-1 derivative is 4 to 8.

11. The transgenic plant or the plant storage organ thereof according to claim 2, wherein the number of linkage of DNA encoding the GLP-1 derivative is 5.

12. The transgenic plant or the plant storage organ thereof according to claim 2, wherein the vector comprises a plant storage organ specific promoter operably linked to a nucleic acid encoding a signal peptide of a plant storage protein and the linked DNA.

13. The transgenic plant or the plant storage organ thereof according to claim 2, wherein the vector comprises the linked DNA inserted in-frame into a nucleic acid encoding a variable region of a plant storage protein.

14. The transgenic plant or the plant storage organ thereof according to claim 2, wherein the plant is a monocotyledon.

15. The transgenic plant or the plant storage organ thereof according to claim 14, wherein the monocotyledon is *Oryza sativa*.

16. The transgenic plant or the plant storage organ thereof according to claim 2, wherein the plant storage organ is a seed.

* * * * *

UNITED STATES PATENT AND TRADEMARK OFFICE
CERTIFICATE OF CORRECTION

| | | |
|---|---|---|
| PATENT NO. | : 7,947,876 B2 | Page 1 of 1 |
| APPLICATION NO. | : 11/662650 | |
| DATED | : May 24, 2011 | |
| INVENTOR(S) | : Koichi Sugita et al. | |

It is certified that error appears in the above-identified patent and that said Letters Patent is hereby corrected as shown below:

On the cover page, the fourth inventor's first name "Humio" should be --Fumio--.

Signed and Sealed this
Seventh Day of August, 2012

David J. Kappos
*Director of the United States Patent and Trademark Office*

SEQUENCE LISTING

```
<160> NUMBER OF SEQ ID NOS: 8

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

His Ser Glu Gly Thr Phe Thr Ser Asp Val Ser Ser Tyr Leu Glu Gly
  1               5                  10                  15

Gln Ala Ala Gln Glu Phe Ile Ala Trp Leu Val Asn Gly Arg
             20                  25                  30

<210> SEQ ID NO 2
<211> LENGTH: 3495
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 2
acagattctt gctaccaaca acttcacaaa gtagtagtca accaaaacta tgctaaggaa         60
tcacctcact tccgcccatg accgtgagca cgactgttca aacagtttgt taatctctac        120
aaagaaggta cactttacct acacaacgcc actaacctga gttacccagc ccatgcaaaa        180
tagccacgtc ttgtgactta agggatttcg cgacaaggca tttcgaaagc ccacacaagg        240
acaccttatg aaaactggag gggtcccaca gaccaacaac aagttaggtc ccaaaccatg        300
ttgtgccagg aaaatccaag gggtcctccc caacaccacc ccgacaaatc cacttgtcca        360
ttggcatcaa gatttgcctg acctagctaa ttactcagcc aggcatgtca caattcaccc        420
atgtggtcac acaccttatg gttggatgaa attctaaagg aatcggtcca tatgagcaag        480
accgagaaac caataccacc agtacttcta ccgaaatacg agtttagtaa actcatttgt        540
tttcaaggca cccgacccag gtgtgtcggg ttttccaggg atttttgtaaa cccaagtttt      600 acccatagtt gatcattcaa attttgagga gggtcattgg tatccgtacc tgagggcacg        660
aatactgaga cctagcattg tagtcgacca aggcggttaa tgcagcaatt gtaggtgggg        720
cctgttggtt tattgcaact gcggccacat ttatgtgtaa tttagagatg tgcattttga        780
```

```
gaaatgaaat acttagtttc aaattagggc tcaaaataat caaaggtgac ctaccttgct      840
tgatatcttg agctttcttc ctcgtattcc gcgcactagg actcttctgg ctccgaagct      900
acacgtggaa cgagataact caacaaaacg accaaggaaa agctcgtatt agtgagtact      960
aagtgtgcca ctgaatgatc tcgattttg aggaatttta aagttgaac agagtcaatc      1020 gaacagacag ttgaagagat atggattttc taagattaat tgattctctg tctaaagaaa      1080
aaaagtatta ttgaattaaa tggaaaaaga aaaggaaaa aggggatggc ttctgctttt      1140
tgggctgaag gcggcgtgtg gccagcgtgc tgcgtgcgga cagcgagcga acacacgacg      1200
gagcagctac gacgaacggg ggaccgagtg gaccggacga ggatgtggcc taggacgagt      1260
gcacaaggct agtggactcg gtccccgcgc ggtatcccga gtggtccact gtctgcaaac      1320
acgattcaca tagagcgggc agacgcggga gccgtcctag gtgcaccgga agcaaatccg      1380
tcgcctgggt ggatttgagt gacacggccc acgtgtagcc tcacagctct ccgtggtcag      1440
atgtgtaaaa ttatcataat atgtgttttt caaatagtta aataatatat ataggcaagt      1500
tatatgggtc aataagcagt aaaaaggctt atgacatggt aaaattactt acaccaatat      1560
gccttactgt ctgatatatt ttacatgaca acaaagttac aagtacgtca tttaaaaata      1620
caagttactt atcaattgta gtgtatcaag taaatgacaa caaacctaca aatttgctat      1680
tttgaaggaa cacttaaaaa aatcaatagg caagttatat agtcaataaa ctgcaagaag      1740
gcttatgaca tggaaaaatt acatacacca atatgcttta ttgtccggta tattttacaa      1800
gacaacaaag ttataagtat gtcatttaaa aatacaagtt acttatcaat tgtcaagtaa      1860
atgaaaacaa acctacaaat ttgttatttt gaaggaacac ctaaattatc aaatatagct      1920
tgctacgcaa aatgacaaca tgcttacaag ttattatcat cttaaagtta gactcatctt      1980
ctcaagcata agagctttat ggtgcaaaaa caaatataat gacaaggcaa agatacatac      2040
atattaagag tatggacaga catttcttta acaaactcca tttgtattac tccaaaagca      2100
ccagaagttt gtcatggctg agtcatgaaa tgtatagttc aatcttgcaa agttgccttt      2160
ccttttgtac tgtgttttaa cactacaagc catatattgt ctgtacgtgc aacaaactat      2220
atcaccatgt atcccaagat gcttttttat tgctatataa actagcttgg tctgtctttg      2280
aactcacatc aattagctta agtttccata agcaagtaca aatagctatg gcgagttccg      2340
ttttctctcg gttttctata acttttgtg ttcttctatt atgccatggt tctatggccc      2400
agcccatggc ccattctgag ggaactttca catctgatgt aagttcttac ctcgagggcc      2460
aagcagctca agaattcatc gcttggctcg taaatggccg tcattctgag ggaactttca      2520
catctgatgt aagttcttac ctcgagggcc aagcagctca agaattcatc gcttggctcg      2580
taaatggccg tcattctgag ggaactttca catctgatgt aagttcttac ctcgagggcc      2640
aagcagctca agaattcatc gcttggctcg taaatggccg tcattctgag ggaactttca      2700
catctgatgt aagttcttac ctcgagggcc aagcagctca agaattcatc gcttggctcg      2760
taaatggccg tcattctgag ggaactttca catctgatgt aagttcttac ctcgagggcc      2820
aagcagctca agaattcatc gcttggctcg taaatggccg tgagctctgt aattgagaac      2880
tagtatcggc gtagagtaaa ataaaacacc acaagtatga cacttggtgg tgattctgtt      2940
cgatatcagt actaaataaa ggttacaaac ttcttcattt tcctacttca tgccatggat      3000
attccattat ggactatagt ggacagggcc ggtcctatga ttttgagggc cctaggcgaa      3060
ctcatcgcga tgggccctcc aagctatata taaaatttat tgatatatat agacgctaat      3120
tttacttgca aaatgaaaac aaatacattc tatatattaa atttaacatt cctggtaatt      3180
```

```
atcaagaaat aaaatcgacc aaaataacaa tatatttgta acttggaact aatataatta    3240
tttattaact taatgaagaa tagaactccg tcatatccat tgcttcctat gaaaagatac    3300
ttcttcgggt atttcttgat gcaaaatcat aaagaacggt attaagatca atagtgtcca    3360
agatatcctt ctcgattgag cacatagcca agccatttaa ccttatttgc gacagttgat    3420
ctcaaatagt ttttcaacaa cttcaatttt gataaactta tttcagctga agctaccatc    3480
ataggaaagt aagag                                                     3495
```

```
<210> SEQ ID NO 3
<211> LENGTH: 182
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 3

Met Ala Ser Ser Val Phe Ser Arg Phe Ser Ile Tyr Phe Cys Val Leu
 1               5                  10                  15

Leu Leu Cys His Gly Ser Met Ala Gln Pro Met Ala His Ser Glu Gly
            20                  25                  30

Thr Phe Thr Ser Asp Val Ser Ser Tyr Leu Glu Gly Gln Ala Ala Gln
        35                  40                  45

Glu Phe Ile Ala Trp Leu Val Asn Gly Arg His Ser Glu Gly Thr Phe
    50                  55                  60

Thr Ser Asp Val Ser Ser Tyr Leu Glu Gly Gln Ala Ala Gln Glu Phe
65                  70                  75                  80

Ile Ala Trp Leu Val Asn Gly Arg His Ser Glu Gly Thr Phe Thr Ser
                85                  90                  95

Asp Val Ser Ser Tyr Leu Glu Gly Gln Ala Ala Gln Glu Phe Ile Ala
           100                 105                 110

Trp Leu Val Asn Gly Arg His Ser Glu Gly Thr Phe Thr Ser Asp Val
       115                 120                 125

Ser Ser Tyr Leu Glu Gly Gln Ala Ala Gln Glu Phe Ile Ala Trp Leu
   130                 135                 140

Val Asn Gly Arg His Ser Glu Gly Thr Phe Thr Ser Asp Val Ser Ser
145                 150                 155                 160

Tyr Leu Glu Gly Gln Ala Ala Gln Glu Phe Ile Ala Trp Leu Val Asn
                165                 170                 175

Gly Arg Glu Leu Cys Asn
            180
```

```
<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Ala Ser Ser Val Phe Ser Arg Phe Ser Ile Tyr Phe Cys Val Leu
 1               5                  10                  15

Leu Leu Cys His Gly Ser Met Ala
            20
```

```
<210> SEQ ID NO 5
<211> LENGTH: 24
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Ala Ser Ile Asn Arg Pro Ile Val Phe Phe Thr Val Cys Leu Phe
 1               5                  10                  15

Leu Leu Cys Asp Gly Ser Leu Ala
            20

<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Ala Ser Lys Val Val Phe Phe Ala Ala Ala Leu Met Ala Ala Met
 1               5                  10                  15

Val Ala Ile Ser Gly Ala Gln
            20

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 7

His His His His His His
 1               5

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Asp Glu Leu
 1
```